United States Patent [19]

Nitecki et al.

[11] Patent Number: 4,797,491
[45] Date of Patent: Jan. 10, 1989

[54] COMPOUND 1-(3-(2-PYRIDYLDITHIO)PROPIONAMIDO)-12-(5-HYDRAZIDOGLUTARAMIDO)-4,9-DIOXADODECANE

[75] Inventors: Danute E. Nitecki; Margaret Moreland, both of Berkeley, Calif.

[73] Assignee: Cetus Corporation, Emeryville, Calif.

[21] Appl. No.: 840,604

[22] Filed: Mar. 17, 1986

[51] Int. Cl.$^4$ .......................................... C07D 213/71
[52] U.S. Cl. ..................... 546/291; 546/294; 546/278; 546/243; 530/395; 560/29; 564/34; 564/149; 564/150; 564/162
[58] Field of Search ............................... 546/291, 243

[56] References Cited

U.S. PATENT DOCUMENTS 4,582,789 4/1986 Sheldon .............................. 435/6

FOREIGN PATENT DOCUMENTS 0088695 9/1983 European Pat. Off. .............. 424/85

OTHER PUBLICATIONS

Taylor, Keith et al., Biochemistry International, 1:4, 353-358, (10/21/80), "A Thiolation Reagent for Cell Surface Carbohydrate".

Primary Examiner—Alan L. Rotman
Attorney, Agent, or Firm—Kate H. Murashige; Gregory J. Giotta; Albert P. Halluin

[57] ABSTRACT

Bifunctional chemicals useful for linking aldehyde containing moieties to moieties containing functionalities which are or can be reactive with sulfhydryl are claimed and have the formula:

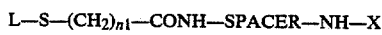

L—S—(CH$_2$)$_{n1}$—CONH—SPACER—NH—X wherein L is a leaving group selected from —H or —S—Ar, wherein Ar represents optionally substituted phenyl or pyridyl;

$n_1 = 2-4$;

X is selected from:
—CO—Y—CONHNH$_2$, a hydrazide;

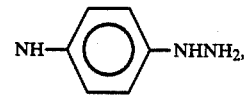

a hydrazine;

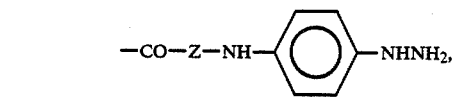

a hydrazine;
—CO—Y—NH—CONHNH$_2$, a semicarbazide; and
—CO—Z—NH—CSNHNH$_2$, a thiosemicarbazide;
wherein Y is alkylene or oxaalkylene and Z is alkylene or a polypeptide residue bridging the N-terminal amino group and C-terminal carboxy group thereof; the SPACER is oxaalkylene or oxaalkylene substituted with hydroxyl and specifically includes residues having formulas selected from

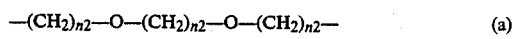

—(CH$_2$)$_{n2}$—O—(CH$_2$)$_{n2}$—O—(CH$_2$)$_{n2}$—   (a)

wherein each n2 is independently 2–4 and

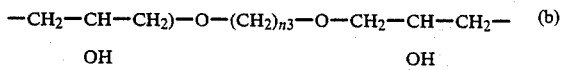

—CH$_2$—CH—CH$_2$)—O—(CH$_2$)$_{n3}$—O—CH$_2$—CH—CH$_2$—   (b)
         |                                    |
         OH                                   OH wherein n3 is 2-6.

Also claimed are hydrazides, semicarbazides, and thiosemicarbazides of ω-mercaptocarboxylic acids which lack SPACER diamine.

1 Claim, No Drawings

COMPOUND 1-(3-(2-PYRIDYLDITHIO)PROPIONAMIDO)-12-(5-HYDRAZIDOGLUTARAMIDO)-4,9-DIOXADODECANE

TECHNICAL FIELD

The invention relates to the preparation and use of cross-linkers for biologically significant moieties. More particularly, the invention relates to heterobifunctional compounds which serve to link aldehyde groups found or created on one biological or other entity to sulfhydryl groups on another.

BACKGROUND ART

There is an extensive literature relating to conjugates of biological significance which are deliberately designed to combine the activities of two previously independent substances. The most prominent example is enzyme linked immunoassay (ELISA), where an enzyme is conjugated to an antibody to serve as a label. Other applications include immunotoxins wherein a toxin is linked with an anitbody to effect the specific delivery of the toxin to a target tissue, delivery of therapeutic agents by linking these agents to antibodies, and reagents for detection or localization of particular tissues by targeting specific tissue receptors with a heteromolecule containing a binding portion and label. A review of such conjugates in tumor therapy appeared in *Immunological Reviews* (1982) 62: 1–216.

A number of approaches to formation of the desired linkages have been employed. Perhaps the most popular approach utilizes the commercially available reagent N-succinimidyl-3-(2-pyridyldithio)propionate (SPDP). SPDP offers the possibility of disulfide bridge between itself and one moiety and an amide between itself and the other. Thus, for example, two proteins can be linked wherein one contains a free amino group with which to form the amide, and another contains a sulfhydryl to form the disulfide. Alternatively, each of two proteins with side chain amino groups can be derivatized with SPDP to provide the needed sulfhydryl functionality for a disulfide bridge between them.

Other available linkers react with protein native or created sulfhydryl groups by using for example a maleimido or haloacetyl group to form a thioether. These linkers generally have the functionality for an amide formation at the opposite end of the linking molecule by providing an activated carboxyl moiety. Thus for example, the activated esters of 6-maleimidocaproic acid, 2-bromoacetic acid, and 2-iodoacetic acid have been used, preferably forming the activated ester form of these acids by generation of the succinimidyl ester or the water soluble ester formed from 1-hydroxy-2-nitro-4-sulfonic acid sodium salt.

Other coupling agents that may be used include the more old fashioned and less specific linkers such as glutaraldehyde and dehydrating agents such as dicyclohexylcarbodiimide.

The foregoing linkers have been chosen with the thought that the two members of the conjugate are both proteins and the known side chain functionality of proteins has been capitalized upon. More recently, it has been realized that if a glycoprotein is one of the components, the sugar moieties of the saccharide portion of the glycoprotein could be employed. This has been suggested, for example, in European Patent Application publication No. 88695, published Sept. 14, 1983. Specifically, among other suggestions, this published application discloses utilization of the carbohydrates present on glycoproteins in general and antibodies in particular by forming hydrazones with the oxidized form of the carbohydrate. The disclosure thus suggests reacting the aldehyde groups of an oxidized antibody saccharide component with a hydrazine reagent or an amine reagent. In that regard, the disclosure envisions using a bifunctional linker having a hydrazine or comparable moiety to the end of a bifunctional linker. No specific linkers containing a hydrazine moiety at one end and a group capable of reaction with sulfhydryl the other are suggested.

However such a specific linker is suggested for the purpose of binding label to cell surface carbohydrates by Taylor, K. E., et al, *Biochemistry International* (1980) 1: 353–358 who suggest the use of 2-acetamido-mercaptobutyric acid hydrazide. This reagent provides an SH group capable of disulfide bond formation with a protein whose own sulfhydryl is activated by, for example, SPDP, and also provides a hydrazide for reaction with the oxidized carbohydrate.

It should be apparent that although there are in the art a number of heterobifunctional linking moieties (referred to by one commercial supplier of these as "double agents"), there is no specific linker class available which provides the capacity for reaction with an aldehyde at one of its termini and reaction to form a disulfide at the other. Such a class of reagents is particularly useful in binding glycoproteins to proteins which have or which can be provided with sulfhydryl groups.

DISCLOSURE OF THE INVENTION

The invention provides a family of heterobifunctional linkers which are designed to facilitate the conjugation of entities which contain oxidized sugars or other aldehyde groups with those which contain functionalities which are, or which can be modified to be, reactive with sulfhydryl. As used in most applicatons, the linkers of the invention should confer reasonable water solubility, be sufficiently flexible to permit some independence in spatial configuration between the two bound moieties, be fairly readily hydrated, and be minimally immunogenic. Of course, not all of these properties need be present in each linker. First, they may not be necessary in the end product depending on the application intended. Second, even if they are required in the end product, it may be possible to confer these properties by additional strategies.

The invention, then, in its primary aspect is directed to compounds of the formula

wherein L is a leaving group selected from —H or —S—Ar, wherein Ar represents optionally substituted phenyl or pyridyl;
$n_1 = 2$–$4$;
X is selected from:
—CO—Y—CONHNH$_2$, a hydrazide;

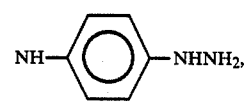

a hydrazine;

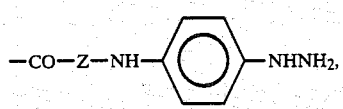

a hydrazine;

—CO—Y—NH—CONHNH$_2$, a semicarbazide; and

—CO—Z—NH—CSNHNH$_2$, a thiosemicarbazide;

wherein Y is alkylene or oxaalkylene and Z is alkylene or a polypeptide residue bridging the N-terminal amino group and C-terminal carboxy group thereof;

the SPACER is oxaalkylene or oxaalkylene substituted with hydroxyl and specifically includes residues having formulas selected from

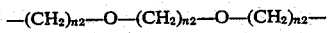

wherein each $n_2$ is independently 2–4 and $$-CH_2-\underset{OH}{CH}-CH_2-O-(CH_2)_{n3}-O-CH_2-\underset{OH}{CH}-CH_2- \quad (b)$$

wherein $n_3$ is 2–6.

The compounds of the invention also include hydrazides, semicarbazides, and thiosemicarbazides of ω-mercaptocarboxylic acids, which thus are similar to the compounds of Formula 1, but which lack SPACER diamine.

In other aspects, the invention relates to processes for synthesis of these linking reagents and to intermediates in these synthetic processes. In still other aspects, the invention relates to the use of these linking reagents to bind appropriate moieties to form conjugates, to the intermediates in such conjugation, and to the conjugates themselves.

Modes of Carrying Out The Invention

The compounds which are the primary focus of the invention contain a functional group capable of reaction with a carbonyl (aldehyde or ketone), at one terminus and a functionality for thio (RS—) linkage to form a disulfide or thioether at the other. The carbonyl-reactive group is selected from hydrazide, hydrazine, semicarbazide, and thiosemicarbazide. The carbonyl-reactive group is separated by a spacer from a residue derived from an ω-mercaptocarboxylic acid.

The S—L Functionality

The sulfhydryl of an ω-mercaptocarboxylic acid group at the disulfide forming functionality of the linker may or may not be derivatized by formation of an intermediate disulfide with optionally substituted pyridyl sulfhydryl or with optionally substituted phenyl sulfhydryl compounds. Both the H of the original mercaptyl group of the ω-sulfhydryl carboxylic moiety and the mercaptopyridyl or mercaptophenyl moiety added by derivatization are leaving groups which are lost in the formation of a disulfide or thioether linkage to one conjugation partner. The use of hydrogen as a leaving group is possible when the group intended to react is itself activated, such as a disulfide; it is also usable when a thioether is be formed by nucleophilic displacement of bromide or iodide ion or by addition to a double bond. If the intended substrate itself contains sulfhydryl with which reaction is intended, a more activated form of the linker is used, and the leaving group is the mercaptoaryl derivative, i.e., mercaptopyridyl or mercaptophenyl.

The most commonly encountered mercaptoaryl is 2-mercaptopyridyl. However, the mercapto group may be situated at the 4 position of the pyridyl moiety and the pyridyl moiety may optionally be substituted with relatively neutral substituents such as one or two lower alkyl (1–4C) groups. Similarly the group symbolized by L may be a mercaptophenyl, optionally substituted with electron-donating substitutents such as methoxy or amino groups. In either case any substituent which does not substantially detract from the ability of the ring to donate electrons to the sulfur of the mercapto group is operable. Thus, in the groups "—S—L", L represents a leaving group which will depart without the electrons of the S—S bond.

The Carbonyl-Reactive Functionality

In preparing the components of the invention the carbonyl-reactive functionality is provided by suitable reaction with the ω-mercaptocarboxylic acid that provides the —S—L group. Thus, the compounds of Formula 1 are combinations of

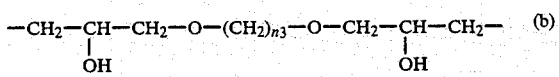

with a variety of suitable reagents.

Embodiments without Spacer

The compounds of the invention can be directly made from the ω-sulfhydryl carboxylic acids without inclusion of spacer by first providing the mercaptoaryl leaving group, if desired, and then converting the carboxyl group to the desired carbonyl-reactive group such as hydrazide. Thus, for these compounds of the invention, Reaction Scheme 1 shown below is used.

Reaction Scheme 1

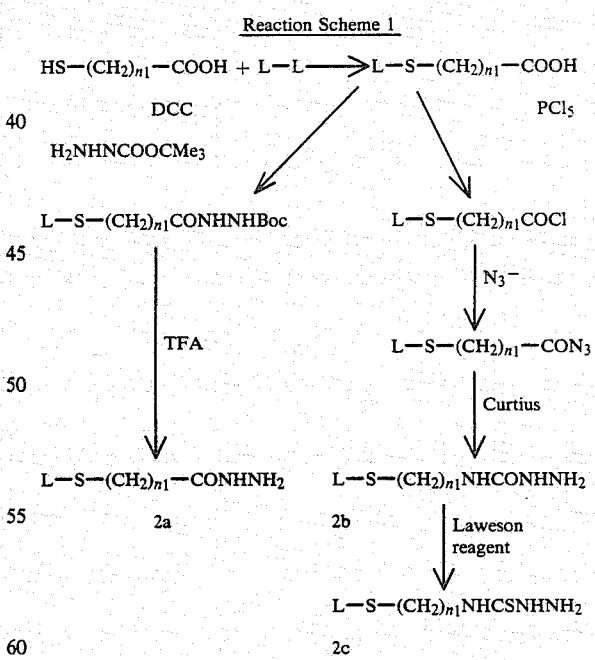

In this scheme to obtain the hydrazide, the derivatized carboxylic acid is reacted with Boc-protected hydrazine. (Boc is a standard abbreviation for tertiary butyloxycarbonyl, a commonly used protecting group in peptide synthesis.) Of course, hydrazine protected by other protecting groups, such as benzyloxycarbonyl, trifluoro acetyl, trityl, or phenyl, may also be used, but Boc is preferred. The reaction can take place in the presence of a dehydrating agent, such as, for example, dicyclohexylcarbodiimide (DCC) or carbonyl-bisimidazole. In the alternative, the carboxylic group can be converted to acyl halide or a reactive ester and then reacted with the protected hydrazine derivative. The protecting group is then removed with suitable reagents, with formic or trifluoroacetic acid in the case of Boc.

For other embodiments, similarly, the semicarbazide is obtained by reaction of the ω-mercaptocarboxylic acid with an acyl activating agent, such as $PCl_5$ or sulfonyl chloride, to obtain the activated carboxyl group, and the reactive carboxyl then treated with sodium azide. The resulting acyl azide is then subjected to the Curtius rearrangement under conditions known in the art to yield the corresponding semicarbazide. This compound of the invention can, in turn, be converted if desired to the thio analog by treating with a suitable reagent for conversion of carbonyl groups to the corresponding thiocarbonyls, such as most preferably, Lawesson reagent. This is also outlined in Reaction Scheme 1 above.

The resulting linker of Formula 2a, 2b or 2c is workable, but its utility is somewhat diminished by the short distance it provides between the conjugated moieties. Therefore, the additional, more complex embodiments including spacer of Formula 1 are also made and are preferred.

The Spacer in General

It is seen from the structures for the exemplary spacer elements of the compound of Formula 1 that the spacer generally contains some hydrophilicity by virtue of inclusion of oxygen, and some flexibility due to its composition as a straight chain rather than including one or more rings. In addition, the spacer is of sufficient length to permit the flexibility required. For those embodiments wherein the carbonyl-reactive functional group is hydrazine or thiosemicarbazide, and wherein the group X includes the polypeptide form of Z, these properties may be conferred at least in part by the nature of Z. For other embodiments these properties, to the extent present, are conferred by spacer. Two particularly preferred exemplary spacers are the oxaalkylene diamines, and the hydroxylated oxaalkylene diamines.

By oxaalkylene is meant saturated hydrocarbon straight chain bivalent moieties in which one or more methylene groups are replaced by oxygen. Thus, exemplary oxaalkylenes include, in addition to those illustrated below, $-CH_2CH_2OCH_2CH_2CH_2-$, $-CH_2OCH_2OCH_2OCH_2-$, $-CH_2OCH_2CH_2CH_2OCH_2-$, $-CH_2OCH_2CH_hd 2OCH_2CH_2OCH_2-$, and $-CH_2OCH_2CH_2CH_2OCH_2CH_2-$.

Embodiments Where Spacer is Derived from a Dioxaalkylene Diamine (a)

A particularly preferred embodiment, whose synthesis is shown in Reaction Scheme 2, provides additional spacing between the two moieties to be conjugated.

Reaction Scheme 2

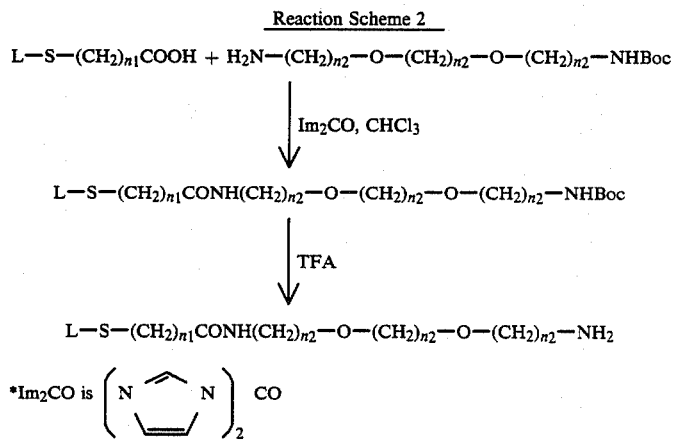

As shown in Reaction Scheme 2, the ω-LS-containing carboxylic acid is reacted with the a suitable monoprotected diamine of a long-chain dioxaalkane. In this illustrative embodiment, the diamine contains two ether linkages separated from each other and from the N-terminal amino groups by straight-chain alkyl groups of varying lengths. Monoprotection is obtained by reacting the diamine with appropriate amino-protecting groups, most preferably activated Boc, and the monoprotected diamines are isolated by chromatography.

The resultant of the dehydration reaction, which is carried out in the presence of standard dehydrating agents, such as any carbodiimide, mixed anhydride, or carbonyl-bis-imidazole, preferably carbonyl-bis-imidazole, is in the protected form. This intermediate is deprotected, in the case of the Boc-protecting group, for example, with trifluoroacetic acid (TFA), as shown.

The product of Reaction Scheme 2 is then reacted with a suitable reagent to provide the carbonyl-reactive functionality as will be described below. Dioxaalkylene diamines which are readily available to prepare this embodiment of the invention, include, for example, 4,9-dioxa-1,12-dodecanediamine. Other suitable oxaalkylene diamines are prepared from polyethylene glycol polymers containing 3-20 monomer units by converting these compounds of the formula:

$$HO-(CH_2CH_2O)_mCH_2CH_2OH,$$

wherein m is 2-19, to the corresponding diamines by methods known in the art per se. A review of such methods is found in Harris, J. M., *Rev Macromol Chem Phys* (1985) 325-373.

Embodiments Derived from Diepoxides (b)

The general procedure for obtaining intermediates to compounds of Formula 1 wherein the spacer is hydroxylated, and which are derived from epoxides, is shown in Reaction Scheme 3.

Reaction Scheme 3

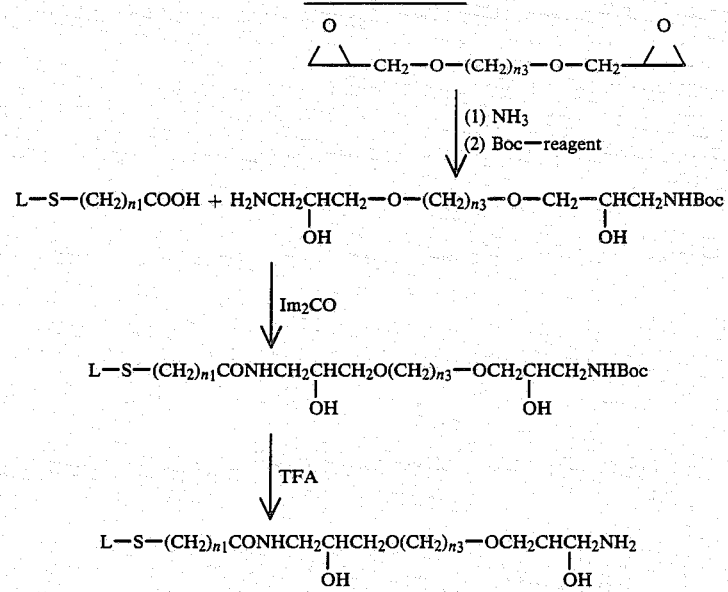

The spacer-containing portion of the molecule derives from a dioxadiepoxide. Typical commercially available dioxaepoxides include 1,4-butanediol diglycidyl ether and ethylene glycol diglycidyl ether.

The synthesis begins by ring opening using ammonia to obtain the corresponding diamine, followed by monoprotection using Boc reagent. The mono protected diamine is separated from the diprotected or unprotected impurities using standard chromatographic or other convenient method. The resulting spacer-containing portion is then reacted with the derivatized ω-mercaptocarboxylic acid in the presence of a dehydrating agent in a manner analogous to that of Reaction Scheme 2 to yield an intermediate having the ability to form disulfide bonds. The carbonyl reactive moiety is added as described below.

Addition of the Carbonyl-Reactive Function

For the preferred spacers and analogous oxaalkylene diamines described above, the intermediate compounds have the generic formula:

$$L-S-(CH_2)_{n1}-CONH-SPACER-NH_2 \qquad (3)$$

and the desired functional group is added by reaction with the primary amine.

For formation of the hydrazide or semicarbazide, an amide linkage is obtained by reaction of the intermediate of Formula 3 with a cyclic anhydride such as glutaric, succinic or glycolic anhydride. This sequence of reactions is shown in Reaction Scheme 4.

Reaction Scheme 4

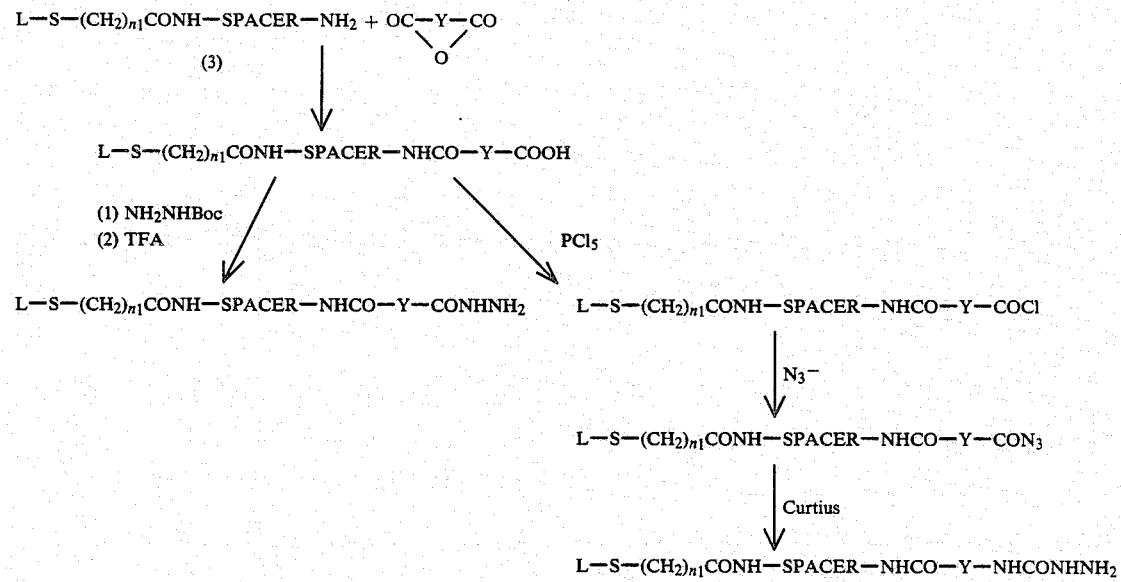

The resulting carboxylic acid is then converted to the hydrazide by reaction with protected hydrazine, or to the semicarbazide by activation, reaction with azide ion to obtain the azide, the Curtius rearrangement to obtain the semicarbazide. The semicarbazide can be converted to the thiosemicarbazide by reaction with Lawsone's reagent; however, this results in the conversion of the amide linkage between the mercaptocarboxylic acid and the spacer to the thioamide. Therefore, it is preferred that the thiosemicarbazide be prepared as described below.

Alternatively, the anhydride may be reacted with monoportected hydrazine or directly with azide ion and condensation with the L—S—(CH$_2$)$_{n1}$CONH—S-PACER—NH$_2$ effected by treating with dehydrating agent in the presence of the compound of Formula 3.

The hydrazine and thiosemicarbazide embodiments of X are prepared according to Reaction Scheme 5:

osemicarbazide, followed by removal of the FM esterifying moiety.

The resulting compounds of Formula 1 are then purified using standard methods and employed as conjugating linkers between compounds containing moieties which are or which can be converted to aldehydes or reactive ketones and compounds containing sulfhydryls or sulfhydryl reactive moieties.

Use as Linkers

The derivatives of the ω-sulfhydryl carboxylic acids and compounds of Formula 1 are useful to provide conjugates between a protein or other compound containing, or able to be converted to contain, carbonyl, usually aldehyde, residues, on the one hand, and com- Reaction Scheme 5

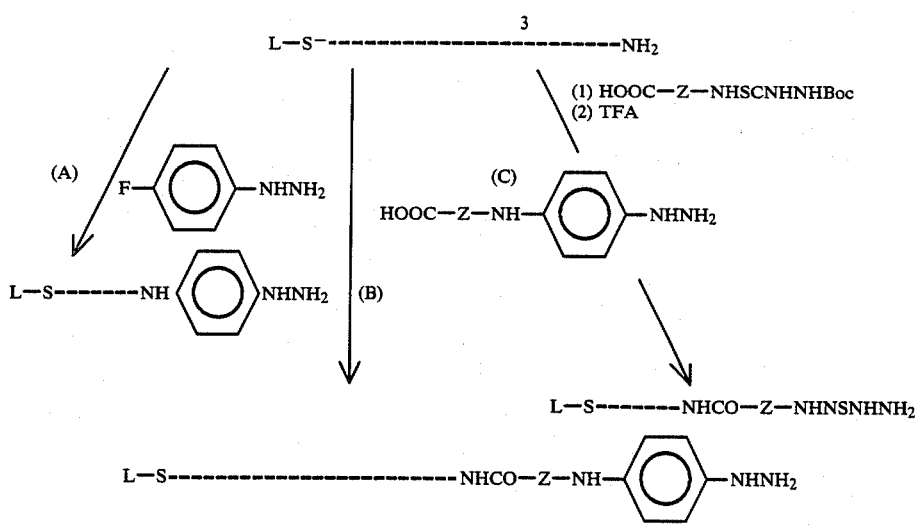

In branch A of Reaction Scheme 5, the intermediate of Formula 3, L—S—(CH$_2$)$_{n1}$—CONH—S-PACER—NH$_2$, is directly reacted with p-fluorophenylhydrazine as described by EP 088695 published 9/14/83, to give the phenylhydrazine derivative. In branch B, the additional sequence designated Z is included by reacting with the p-fluoro-phenylhydrazine a compound of the general formula H$_2$N—Z—COOH to obtain the analogous reagent for amide formation with the intermediate of Formula 3. Convenient choices for Z include amino acids in general, but are more preferably polypeptides which can thus provide additional spacer function, including hydrophilicity and flexibility. For instance, poly-L-serine or poly-L-glycine might be used. The polypeptide need not be a homopolymer, but the amino acid residues should be chosen so that water solubility is maintained, and so that there is not a multiplicity of reactive centers—e.g., poly-L-glutamic acid may not be a workable choice.

In the C branch of Reaction Scheme 5, the intermediate of Formula 3 is reacted with the compound of the formula: HOOC—Z—NHCSNHNHBoc, which is prepared from a compound of the formula HOOC—Z—NH$_2$ in several steps. The carboxylic acid group is first protected with a suitable easily removable esterifying group such as 9-fluorene methyl (FM), and the protected compound is then reacted to obtain the corresponding thiocyanate (—SCN). The thiocyanate is then reacted with protected hydrazine to obtain the thipounds capable of forming disulfide linkages, on the other. The conjugation is conducted by reacting the linker with the carbonyl, followed by conversion to the new disulfide or thio ether. The details of the reaction conditions depend on the specific moieties used, and are understood in the art.

For a particularly preferred embodiment wherein immunoglobulins are the source of aldehydes, preliminary oxidation of the glycoprotein is necessary. The immunoglobulin is treated with sodium periodate or other suitable oxidizing agent at appropriate pH (for periodate, about 6.5) in the dark, for one hour. After the oxidation, the reaction mixture is separated on a sizing gel and treated with the linker of the invention in aqueous solution (pH about 5) for 1–5 hours, generally around 2 hours. After desalting, the extent of reaction is measured by analysis of pyridine-2-thione release after reduction with DTT by measuring the adsorbance at 343 nm. The hydrazone, semicarbazone, or thiosemicarbazone formed may be stabilized by reduction with a suitable reducing agent, such as sodium borohydride, or, preferably, sodium cyanoborohydride.

The derivatized immunoglobulin is then treated (pH about 8) with a sulfhydryl-containing moiety, such as, for example, ricin A chain or other protein-containing free SH groups. The derivatized immunoglobulin and sulfhydryl-containing moiety are used in a ratio of approximately 1:2, and a solubilizing agent, such as propylene glycol, added to prevent precipitation. The conjugates are then purified on suitable columns, such as sizing gels, for use as immunotoxins.

EXAMPLES

The following examples are intended to illustrate, but not to limit, the invention.

EXAMPLE 1

Preparation of
1-[3-(2-pyridyldithio)propionamido]-12-[5-hydrazido-glutaramido]-4,9-dioxadodecane The synthesis of the title compound is outlined in Reaction Schemes 1, 2 and 4. The starting material, 3-(2-pyridyldithio)propionic acid, was prepared by reaction of 3-mercaptopropionic acid with 2-pyridyl disulfide in ethanol and purified by chromatography on alumina, followed by recrystallization from water and from toluene. The other starting material, monoprotected 4,9-dioxa-1,12-dodecanediamine, was prepared by reaction of the diamine with 2-(tert-butyloxy-carbonyloxyimino)-2-phenylacetonitrile (Boc-ON) (Aldrich) in methanol and purified by extraction and preparative low-pressure chromatography on silica gel.

The 3-(2-pyridyldithio)propionic acid was dissolved in chloroform and one equivalent of carbonyldiimidazole was added. After about 20 min, when carbon dioxide evolution ceased, 1 equivalent of the monoprotected diamine was added. The reaction was followed by TLC. The reaction was complete in 2 hr, and the product was purified by chromatography on silica gel. The yield was 74%. The Boc protecting group was removed by treatment with trifluoroacetic acid (TFA) at room temperature for 1 hr and the TFA removed by evaporation under vacuum.

The intermediate compound, corresponding to Formula 3 was dissolved in acetonitrile, and triethylamine was added to neutralize residual TFA. The protected glutaric acid monohydrazide, which had been prepared by reaction of glutaric anhydride and t-butylcarbazate in methanol and recyrstallized from chloroform-toluene in 60% yield, was added in an amount equivalent to the diamine-containing intermediate. One equivalent of 1-ethyl-3-(3'-dimethylaminopropyl)-carbodiimide (EDC) was added and the mixture stirred overnight at room temperature. The solvent was evaporated and the residue partitioned between ethyl acetate and water. The ethyl acetate solution was washed with aqueous acid and aqueous base and evaporated. The protected form of Formula 1 was purified by chromatography on silica gel to obtain a yield of 25% for this reaction. The protecting Boc group was removed by treatment with TFA at room temperature for 2 hr following which the TFA was removed under vacuum, and the residue was redissolved in methanol and reevaporated. The product of Formula 1, a slightly yellow oil nicknamed "Alice", was stored in a desiccator at room temperature.

EXAMPLE 2

Conjugation of Antibody and RTA with Linker

IgG 280D11, a monoclonal antibody reactive with breast tumor antigen (33.3 mg/ml in PBS, pH 7) was used. For oxidation, to 2 ml of this solution, a 100 mM solution of sodium metaperiodate in 440 mM NaOAc, pH 5.5, freshly made, was added in 25-fold excess in the dark at room temperature. After 1 hr of incubation the reaction mixture was passed through a 100 ml column of Bio-Gel P-6DG (Bio-Rad) in 0.01M sodium phosphate, 0.15M NaCl, pH 4.85. Fractions of oxidized IgG 280D11 were combined without further concentration.

Thirty mg of linker prepared in Example 1 were dissolved in 0.6 ml of deionized water and added in 100-fold excess to the oxidized IgG mixture. After 2 hr of incubation and occasional swirling, the reaction mixture was run through a 100 ml column of P6DG in 0.1M sodium phosphate, 0.01M EDTA, pH 8. Fractions of IgG were combined and an aliquot analyzed for pyridine-2-sulfide release (P2T) by measuring the absorbance at 343 nm after reduction with DTT. The ratio of P2T per derivatized IgG was 2.8.

For coupling to ricin A (RTA) the derivatized antibody was concentrated to 4.8 mg/ml in the same buffer using a Centricon Amicon Microconcentrator. Preliminary analysis of the RTA preparation using 5,5'-dithiobis(2-nitrobenzoic acid) (DTNB) and absorbance at 412 nm showed 0.79 SH moieties per RTA molecule. Nine ml of the 4.8 mg/ml concentrated IgG (43.7 mg) were added to 13 ml of 5.5 mg/ml RTA (71.5 mg). Propylene glycol (5%) was added to prevent precipitation, and after 1.5 hr the mixture was diluted with an equal volume of buffer and propylene glycol increased to 20%. The final concentrations of immunoglobulin and RTA in the mixture were 0.8 mg/ml and 1.3 mg/ml, respectively. The conjugation mixture was kept at room temperature for 3 hr and in the refrigerator overnight. Gel electrophoresis on 6.5% polyacrylamide gel showed the formation of conjugates. The conjugates were purified by chromatography over a Sephacryl S-200 column in phosphate buffered saline to remove unreacted RTA and then chromatographing the conjugate and unreacted antibody mixture on Phenyl-Sepharose CL-4B (Pharmacia), using a 5%–30% propylene glycol gradient. Free antibody and conjugate were well separated. The results of several conjugation reactions are shown in Table 1.

TABLE 1

| Experiment | Materials Used in Each Experiment | | | |
| --- | --- | --- | --- | --- |
| | 1 | 2 | 3 | 4 |
| IgG 280D11 | 3.9 mg | 3.9 mg | 66 mg | 65 mg |
| NaIO4 (0.1 M) | 10 μl | 10 μl | 222 μl | 222 μl |
| Alice | 5 mg | 5 mg | 60 mg | 30 mg |
| Alice IgG | 3.5 | 2.2 | 3.1 | 2.8 |
| RTA | 1.85 mg | 1.26 mg | 59 mg | 70 mg |
| $\frac{[SH]}{[RTA]}$ | 0.87 | 0.27 | 0.88 | 0.79 |
| [IgG] in conj. mixture | 1.1 mg/ml | 0.5 mg/ml | 2.2 mg/ml | 0.8 mg/ml |
| [RTA] in conj. mixture | 1.62 mg/ml | 1.65 mg/ml | 3.4 mg/ml | 1.3 mg/ml |
| SH/Linker | 1.8 | 1.8 | 2.2 | 2.2 |
| Total volume of conjugate | 1.05 ml | 2.25 ml | 20.5 ml | 53.4 ml |
| Conjugate recovered | | | | 51 mg |
| Yield | | | | 65% |

Recovery and percent yield are shown only in column 4 because the conjugate was purified in that case, thus permitting accurate determination of these values. However, similar results were also obtained in columns 1–3 based on assessment of unpurified material.

EXAMPLE 3

Linkage followed by Reduction

The procedure for coupling of the linker to IgG was followed as set forth in Example 2, except that one hour after the addition of linker to IgG, sodium cyanoborohydride was added in equimolar amount to linker, and the mixture incubated for an additional hour. Then 5,5'-dithiobis(2-nitrobenzoic acid) (DTNB) was aded, the pH adjusted to 7, and the reaction continued for 0.5 hours. IgG containing fractions obtained by applying the mixture to Biogel P6DG in 0.1M phosphate, 0.01M EDTA, pH8 and eluting were combined and analyzed for TNB release by measurement of absorption at 412 nm after reduction with DTT. The IgG-conjugated linker was then used to bind RTA as described in Example 2.

EXAMPLE 4

Control Conjugation with Alternate Linkers

Similar conjugates made with ricin toxin A and immunoglobulin using the hydrazide of Scheme 1, Formula 2a, 2b or 2c, or the 2-acetamino-4-thiobutyric hydrazide of Taylor and Wu, were prepared using the foregoing procedure, but yields were less than 1%.

We claim:

1. The compound 1-(3-(2-pyridyldithio)propionamido)-12-(5-hydrazidoglutaramido)-4,9-dioxadodecane.

* * * * *